(12) United States Patent
Ridenour et al.

(10) Patent No.: US 7,930,131 B2
(45) Date of Patent: Apr. 19, 2011

(54) ANALYZING FOOT PRESSURE OF A BOWLER

(75) Inventors: Paul J. Ridenour, Waukesha, WI (US);
Neil B. Stremmel, Grand Prairie, TX (US); Bill Monce, Wheaton, IL (US);
James E. Jaryszak, Mansfield, TX (US)

(73) Assignee: United States Bowling Congress, Inc., Arlington, TX (US)

( * ) Notice: Subject to any disclaimer, the term of this patent is extended or adjusted under 35 U.S.C. 154(b) by 95 days.

(21) Appl. No.: 12/360,130

(22) Filed: Jan. 27, 2009

(65) Prior Publication Data

US 2009/0204360 A1 Aug. 13, 2009

Related U.S. Application Data

(60) Provisional application No. 61/027,700, filed on Feb. 11, 2008, provisional application No. 61/027,697, filed on Feb. 11, 2008.

(51) Int. Cl.
*G01L 5/00* (2006.01)
*A63B 69/00* (2006.01)
*A63D 5/00* (2006.01)

(52) U.S. Cl. .......................... 702/139; 434/249; 473/55
(58) Field of Classification Search .................. 702/139; 434/249; 473/55
See application file for complete search history.

(56) References Cited

U.S. PATENT DOCUMENTS

| 3,323,367 A | 6/1967 | Searle |
| 3,897,058 A | 7/1975 | Koch |
| 4,861,034 A | 8/1989 | Lee |
| 5,033,291 A | 7/1991 | Podoloff et al. |
| 5,118,112 A | 6/1992 | Bregman et al. |
| 5,221,088 A | 6/1993 | McTeigue et al. |
| 5,251,903 A | 10/1993 | Bixler et al. |
| 5,316,479 A | 5/1994 | Wong et al. |
| 5,322,289 A | 6/1994 | Abrams et al. |
| 5,343,445 A | 8/1994 | Cherdak |
| 5,372,365 A | 12/1994 | McTeigue et al. |
| 5,419,563 A | 5/1995 | Abrams et al. |
| 5,431,395 A | 7/1995 | Ganger, Sr. |
| 5,542,676 A | 8/1996 | Howe, Jr. et al. |
| 5,878,378 A | 3/1999 | Brommer et al. |
| 5,885,229 A * | 3/1999 | Yamato et al. ................. 600/592 |
| 5,957,870 A | 9/1999 | Yamato et al. |
| 6,231,527 B1 | 5/2001 | Sol |
| 6,441,745 B1 | 8/2002 | Gates |
| 6,567,536 B2 | 5/2003 | McNitt et al. |
| 6,616,556 B1 | 9/2003 | Osmudsen |
| 6,716,034 B2 | 4/2004 | Casanova, Jr. et al. |

(Continued)

OTHER PUBLICATIONS

"Bowling Execution" John Jowdy. 2nd Ed. Human Kinetics Books, 2002.*

*Primary Examiner* — Jonathan C. Teixeira Moffat
(74) *Attorney, Agent, or Firm* — Michael Best & Friedrich LLP

(57) ABSTRACT

Systems and methods for measuring and analyzing the pressure distribution on the foot of a bowler. Methods are taught for analyzing a bowler's performance. In some embodiments, the bowler performs a plurality of bowling motions. The distribution of pressure exerted on the foot are measured and recorded at regular time intervals. The bowler's performance is evaluated based upon the recorded pressure distributions. Methods are also taught for using recorded foot pressure distribution data to fit a bowler with proper footwear.

15 Claims, 6 Drawing Sheets

U.S. PATENT DOCUMENTS

| | | |
|---|---|---|
| 6,807,869 B2 | 10/2004 | Farringdon et al. |
| 6,836,744 B1 | 12/2004 | Asphahani et al. |
| 6,905,339 B2 | 6/2005 | DiMare et al. |
| 7,089,152 B2 | 8/2006 | Oda et al. |
| 2003/0054327 A1* | 3/2003 | Evensen .................. 434/252 |
| 2007/0001106 A1* | 1/2007 | Schmidt et al. ............ 250/225 |
| 2007/0026974 A1* | 2/2007 | Marty et al. .............. 473/467 |
| 2008/0242437 A1* | 10/2008 | Taylor ...................... 473/269 |

* cited by examiner

US 7,930,131 B2

ANALYZING FOOT PRESSURE OF A BOWLER

RELATED APPLICATIONS

This patent application claims priority to U.S. Provisional Patent Applications Ser. Nos. 61/027,700, filed Feb. 11, 2008, and 61/027,697, filed Feb. 11, 2008, the entire contents of which are both herein incorporated by reference.

FIELD OF INVENTION

The invention relates generally to methods and systems for athletic training and performance analysis of bowlers and, in particular, to methods and systems for measuring and analyzing foot pressure during a bowling motion.

BACKGROUND

Systems are known that analyze different aspects of the human gait and plantar pressure distribution. Some previous systems have been used in sports such as golf or skiing to monitor balance.

SUMMARY

While some attempts have been made to analyze gait and plantar pressure in other sports, detailed analysis of plantar pressure distribution during bowling motions has, in general, not been conducted. Bowling coaching has generally been limited by what can be perceived by human senses. However, the fluid motion of an ideal bowling movement can be greatly affected by changes in balance and foot pressure that are not perceptible to a human. As such, coaches and equipment fitters have been limited in their ability to coach and fit bowlers.

Some embodiments of the invention provide methods of analyzing a bowler's performance. A bowler performs a first bowling motion while the distribution of pressure exerted on the sole of his foot is measured. These measurements are recorded at regular time intervals to create a set of pressure distribution frames. In some embodiments, the bowler performs a second bowling motion to create a second set of pressure distribution frames. The bowler's performance is evaluated based upon the first set of pressure distribution frames and, in some embodiments, the second set of pressure distribution frames.

Some embodiments provide methods of fitting a bowler with appropriate equipment. In some such embodiments, a bowler performs a first bowling motion with a first bowling shoe while the pressure distribution exerted on the sole of his foot is measured. These measurements are recorded at regular time intervals to create a set of pressure distribution frames. The fit of the first bowling shoe for the particular bowler is evaluated based upon the set of pressure distribution frames.

In some embodiments for fitting the bowler with appropriate equipment, the bowler performs a second bowling motion with a second bowling shoe to create a second set of pressure distribution frames. The fit of the first bowling shoe is evaluated by comparing the first set of pressure distribution frames to the second set of pressure distribution frames. In some embodiments, the bowler performs a plurality of bowling motions with the first bowling shoe and a plurality of bowling motions with the second bowling shoe. In some embodiments, the fit of the first bowling shoe is evaluated by comparing the consistency of the pressure distribution sets for the first bowling shoe to the consistency of the pressure distribution sets for the second bowling shoe.

Some embodiments provide methods of evaluating athletic footwear for a specific athletic activity. An athlete performs an athletic motion related to the specific athletic activity while wearing a first athletic shoe equipped with a plantar pressure distribution sensor. The distribution of pressure exerted on the sole of the athlete's foot during the first athletic motion is measured and is recorded at regular time intervals. The athlete then performs the athletic motion a second time while wearing a second athletic shoe equipped with a plantar pressure distribution sensor. The distribution of pressure exerted on the sole of the athlete's foot is again recorded at regular time intervals. The recorded data from the first shoe is then compared to the recorded data from the second shoe.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
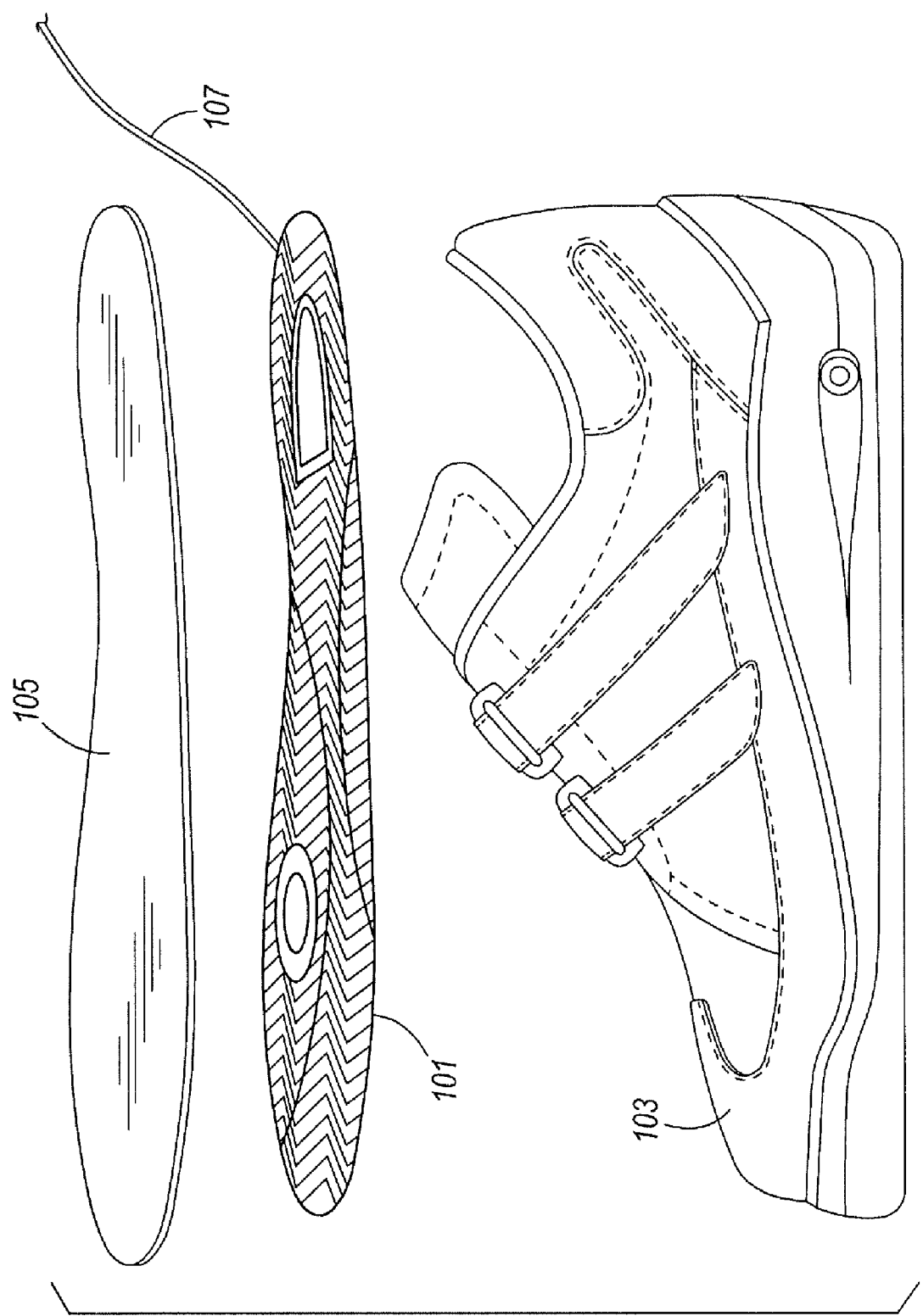
FIG. 1 is an exploded view of one construction of a shoe fitted with a plantar pressure sensor.

FIG. 1 illustrates one construction of a shoe fitted with a plantar pressure distribution sensor 101. Plantar pressure distribution sensor 101 is inserted into shoe 103 underneath insole 105. Insole 105 holds the plantar pressure distribution sensor 101 in place and prevents the bowler's foot from causing the sensor to move or wrinkle during use. Plantar pressure distribution sensor 101 includes a two-dimensional array of pressure sensors arranged as a flat surface. As discussed in detail below, the sensor arrangement allows for detailed data acquisition across the surface of the foot. Cable 107 communicates data acquired from the plantar pressure distribution sensor 101. A suitable commercially available system of sensors is the F-Scan® VersaTek® System from Tekscan, Inc.

Figure 2:
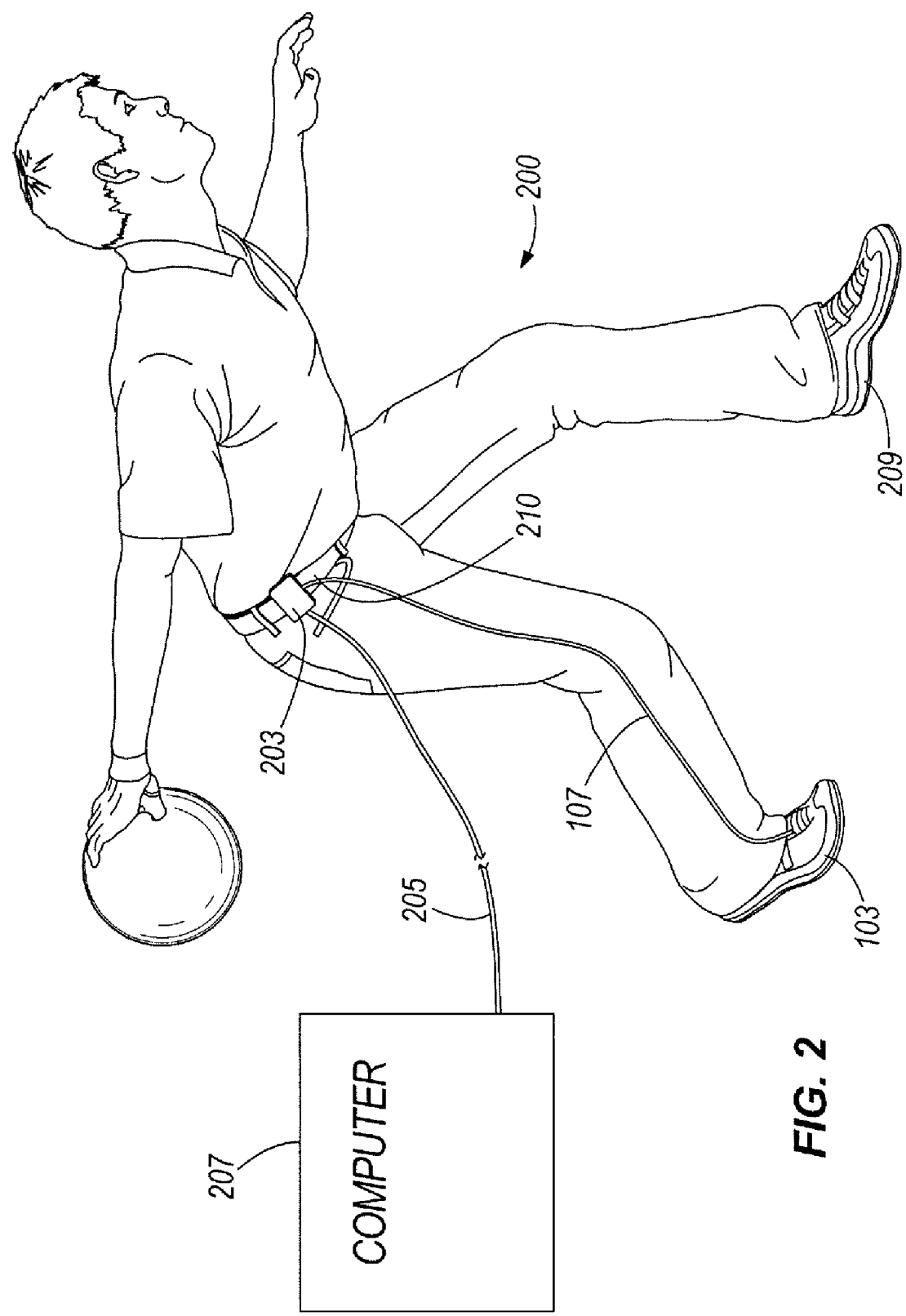
FIG. 2 is an illustration of interconnections of the plantar pressure sensor of FIG. 1 as worn by a bowler and a computerized pressure monitoring system according to one construction.

FIG. 2 shows a bowler 200 wearing the shoe equipped with the plantar pressure distribution sensor 101 and associated monitoring equipment according to one construction. As discussed above in reference to FIG. 1, cable 107 is connected to plantar pressure distribution sensor 101 and communicates data acquired by the sensor 101. Cable 107 extends from the shoe 103 and connects to communication device 203. Communication device 203 is further connected to a computer 207 through cable 205. When the bowler performs a bowling motion, communication device 203 receives pressure measurement data from the pressure sensor 100 and sends it to computer 207 where it is displayed, interpreted, and analyzed. In some embodiments, the other shoe worn by bowler 200, shoe 209, is fitted with similar monitoring equipment (not pictured) to allow for the monitoring and analysis of the plantar pressure distribution on both feet.

The system shown in FIG. 2 may be modified in a variety of ways. For example, in some constructions, communication device 203 is worn on a belt 210 (as pictured in FIG. 2) while, in other constructions, it is strapped to the ankle of the bowler. In some constructions, communication device 203 sends data to computer 207 through wireless means such as a radio frequency (RF) link. In some constructions, computer 207 is a general-purpose computer such as a desktop personal computer. In other constructions, computer 207 it is a special purpose device, such as a device with a specialized processor (e.g., an ASIC) designed specifically to monitor and analyze foot pressure.

Figure 3:
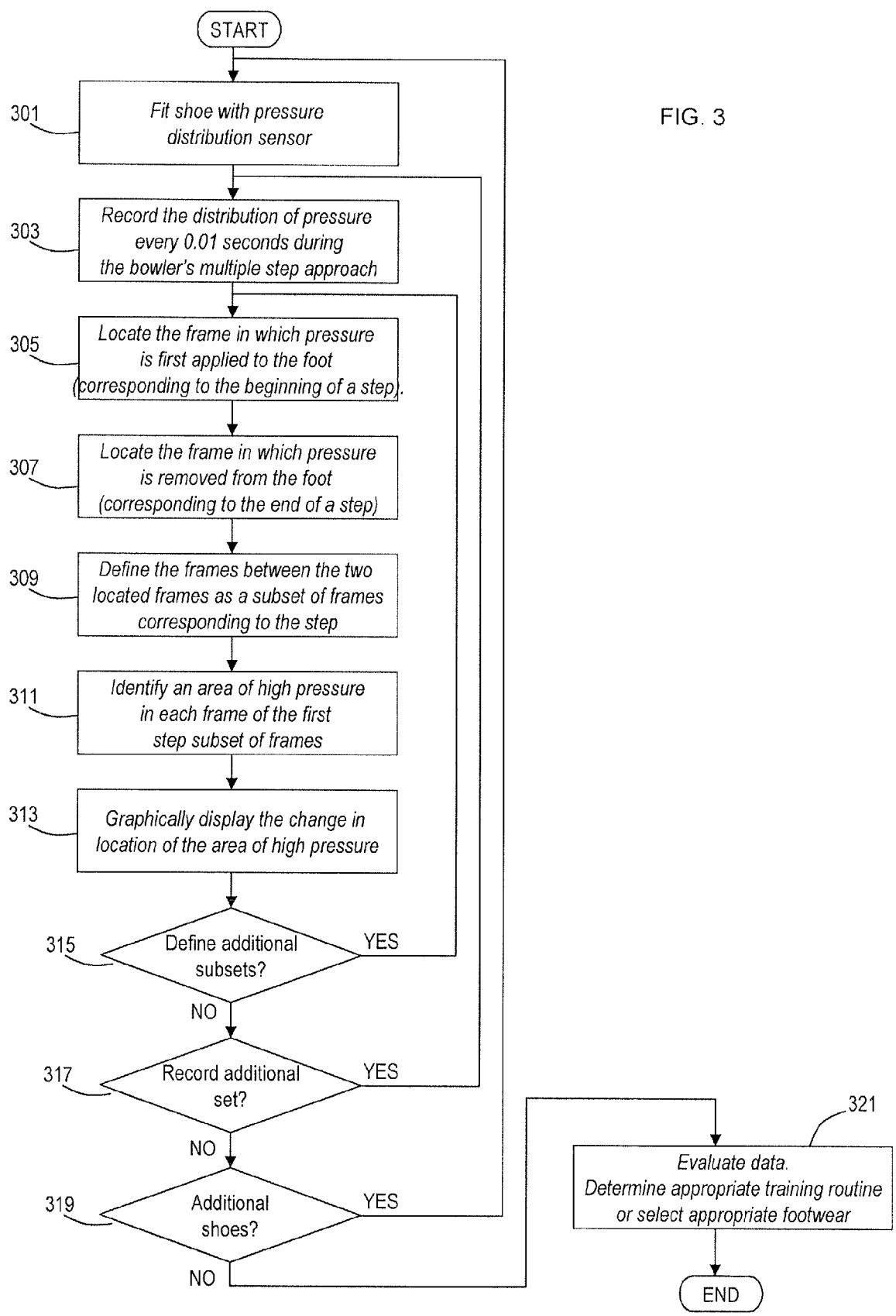
FIG. 3 is a flow chart illustrating a process of recording and analyzing pressure data.

FIG. 3 illustrates a method of recording and analyzing the data captured by the system shown in FIG. 2. At block 301, a shoe is fitted with a pressure distribution sensor as shown in FIG. 1. The bowler then performs a multiple step approach. In some of the examples illustrated herein, the bowler utilizes a four-step approach. In others, a five-step approach is used. The methods and systems described herein may be applied to a four-step approach, a five-step approach, or other style of bowling approach. At block 303, the distribution of pressure detected by the pressure sensor is recorded every 0.01 seconds (100 frames per second) during the bowler's approach and release. The recorded frames are stored as a first set of pressure distribution frames.

From the first set of pressure distribution frames, a subset of frames can be identified corresponding to each step in the bowler's approach. At block 305, a frame is located where pressure is first applied to the foot. This frame corresponds to the beginning of the step. At block 307, a frame is located where pressure is removed from the foot. This frame corresponds to the end of the step. At block 309, the series of frames between these two is defined as a subset of frames corresponding to the step. At block 311, an area of high pressure is identified in each frame in the subset of frames. At block 313, a line is plotted across an image of the bowler's foot showing how the area of high pressure moves throughout the step. The area of high pressure provides quantitative information about how the bowler balances his weight and how this balance changes throughout the step. The identification of subsets can be repeated for each step in the bowler's four-step approach (block 315).

As described in examples below, the bowler or coach may analyze the bowler's performance by capturing and evaluating multiple sets of pressure distribution frames. At block 317, the method may be repeated from block 303 until the desired number of sets of pressure distribution frames has been captured. In other examples (some of which are described below), an equipment fitter may use this method to evaluate and select footwear for a bowler. In such examples, the method may be repeated from block 301 until the desired number of sets of pressure distribution frames has been captured for each set of footwear (block 319). When all desired data has been captured, the bowler or coach evaluates the sets of pressure distribution frames and the subsets identified within each set. Based upon this evaluation, the bowler or coach may determine an appropriate training routine (block 321).

Figure 4:
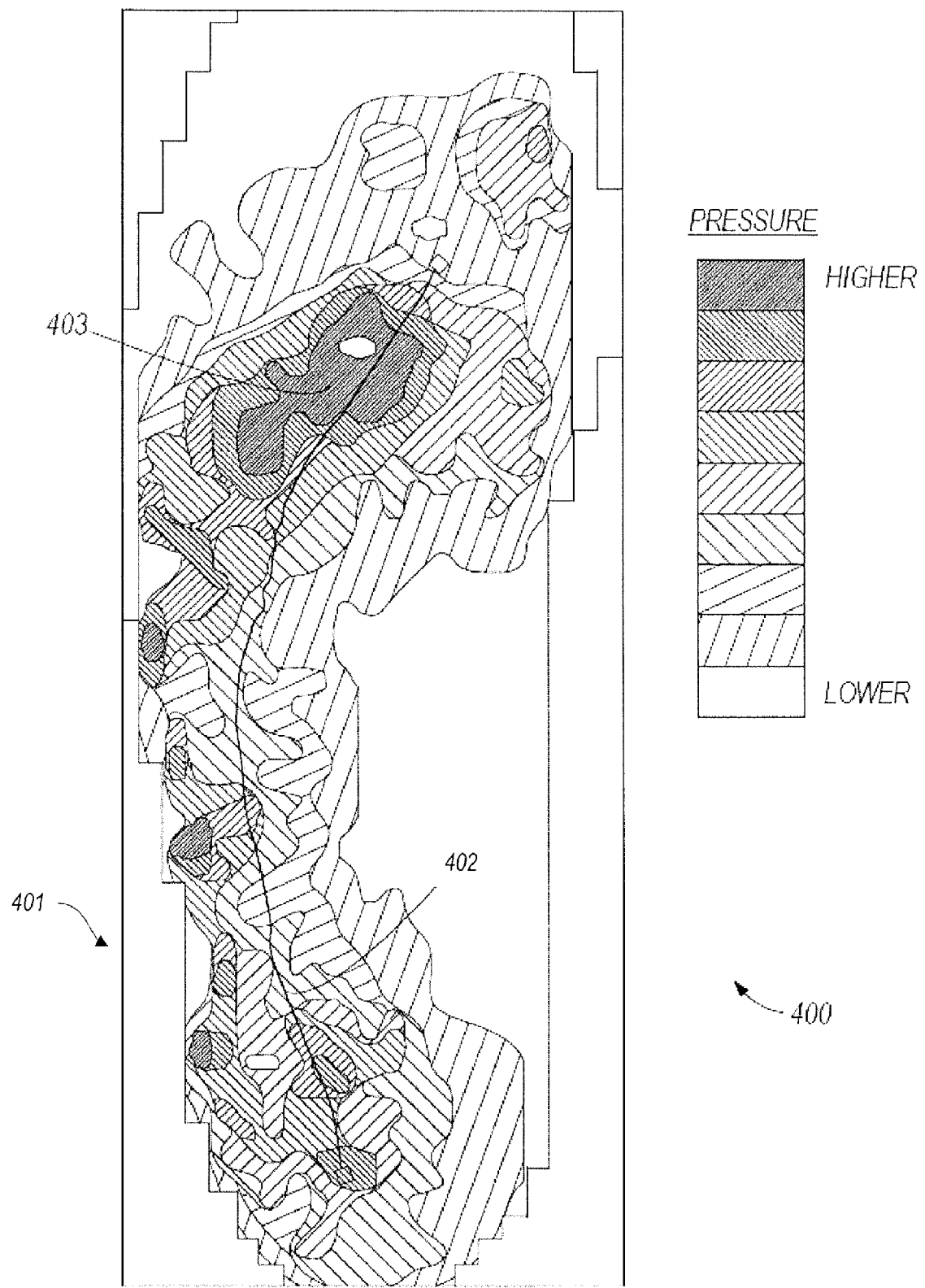
FIG. 4 is an illustration of one construction of a graphical display showing pressures recorded by the system of FIG. 2.

FIG. 4 is an example of a graphical display 400 that is displayed by the computer 207 (FIG. 2). The display 400 includes an image 401 illustrating one frame of pressure data detected by sensor 101 (FIG. 1) toward the end of a bowler's power step. The "power step" refers to the second to last step taken by a bowler during his approach and occurs immediately before the "slide step." The plantar pressure distribution during this step provides useful information about the position and balance of the bowler's body. At the time that the frame of pressure data was captured, a large amount of pressure was being applied to the center of the ball of the bowler's foot (area 403). Line 402 illustrates how the area of high pressure (area 403) moved across the foot in preceding pressure distribution frames and indicates that the bowler's weight was centered and balanced as the bowler rolled his foot from heel to toe.

FIG. 4 illustrates one pressure distribution frame captured by the system of FIG. 2 according to the method of FIG. 3. This pressure distribution frame was recorded toward the end of a bowler's power step. The "power step" refers to the second to last step taken by a bowler during his approach and occurs immediately before the "slide step." The display 400 includes an image of a foot 401, and illustrates one frame of pressure data for the foot. At the time that the frame of pressure data was captured, a large amount of pressure was being applied to the center of the ball of the bowler's foot (area 403). Line 402 illustrates how area 403 moved across the foot in preceding pressure distribution frames and indicates the bowler's weight was centered and balanced as the bowler rolled his foot from heel to toe.

Figure 6:
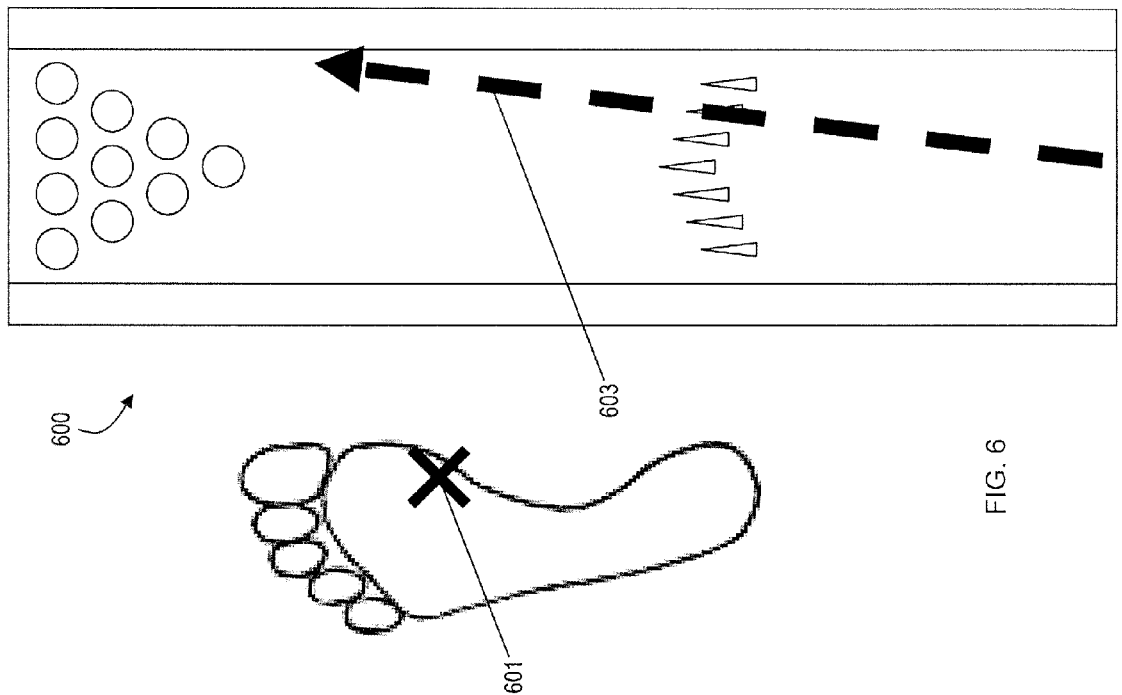
FIG. 6 is an illustration of one example of how off-centered pressure distribution during the bowler's power step affects the direction of the bowling ball after release.
Figure 5:
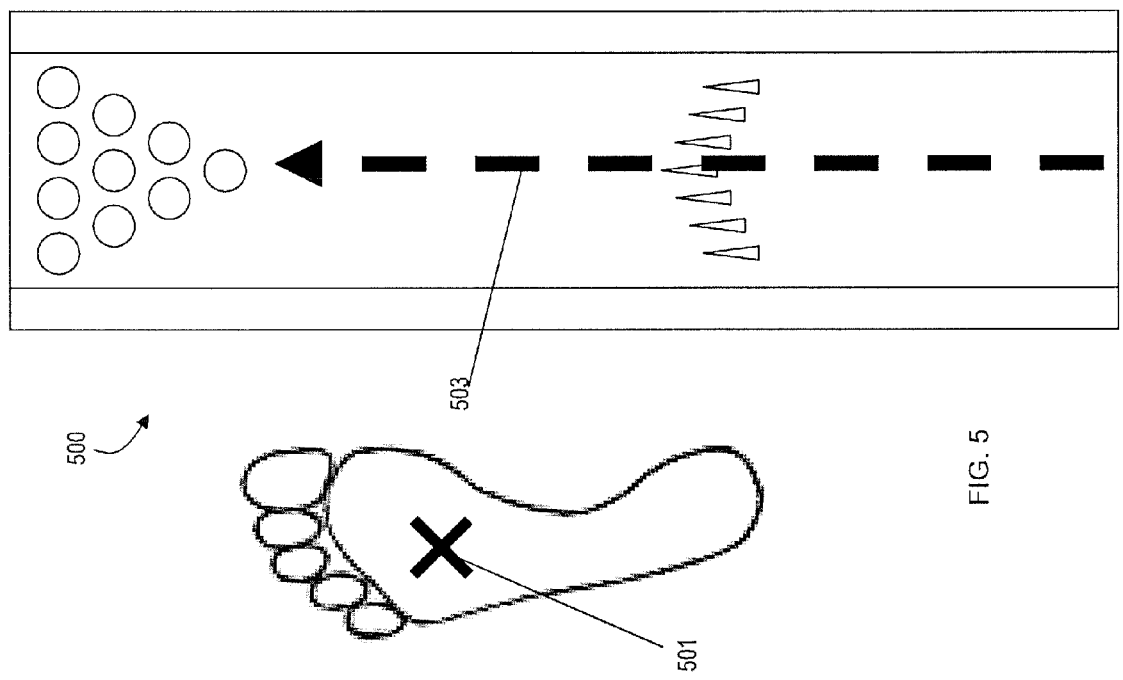
FIG. 5 is an illustration of one example of how pressure distribution during the bowler's power step affects the direction of the bowling ball after release.

FIGS. 5 and 6 demonstrate examples of how pressure distribution data, such as the data displayed in FIG. 4, can be used by a bowling coach. Many factors during the bowler's approach and release affect the direction and movement of a bowling ball after it is released. As discussed in co-pending U.S. patent application Ser. No. 12/360,155, the position and pressure of the bowler's grip affect the direction, rate of rotation, and angle of rotation among other things. Similarly, minor variations in foot pressure affect the ball's performance. Such variations, however, are not easily perceptible to the human senses. As a consequence, it is difficult for a bowling coach to determine whether the inconsistent performance of a bowler is due to problems in the grip, the foot pressure, or another variable.

Consider the following example. A bowler comes to a coach. She usually plays a straight line and is fairly consistent in throwing the bowling ball down the center of the lane. However, occasionally the ball veers toward the right. She wants to identify the cause of these erratic throws and work to prevent them in the future. The bowling coach fits her with the system of FIG. 2 and instructs her to throw the ball ten times using her normal approach.

Although the majority of the bowler's throws traveled straight down the center of the lane 500 (such as path 503 in FIG. 5), two throws were angled to the right of the lane 600 (such as path 603 in FIG. 6). The bowling coach then analyzes the recorded pressure data. In the straight, centered throws 503, the coach observes an area of high pressure 501 at the center of the ball of the bowler's foot toward the end of the power step. In the inconsistent, off-centered throws 603, the area of high pressure 601 appears toward the inside of the bowler's foot.

The coach concludes that the bowler's balance and position during the power step is the cause of the errant throws. This might be affected by several factors. For example, she may be opening her shoulders more during her power step, causing her weight to shift and her throw to be angled outward. Also, for example, she may be stepping too far to the left during her power step. To compensate, her weight shifts more during her slide step and the ball is angled outward. Whatever the cause of the off-centered pressure, the coach determines from the recorded pressure data that his instruction should begin by focusing on the bowler's power step and not on, for example, her grip on the bowling ball.

Every bowler's style of play is different. A coaching method that works for one bowler may not be appropriate for and, in fact, may be detrimental to another bowler. The plantar pressure data, such as displayed in FIG. 4, is also used by a bowling coach to identify the bowler's natural tendencies and to customize coaching drills and training programs based upon those tendencies. For example, a novice bowler is observed exerting a substantial amount of pressure on the front of the ball of the foot near the toes during the power step. The bowler is pushing forward with a large amount of force going into the slide step and might be naturally suited for a high speed throwing style. Based upon plantar pressure data recorded by the system of FIG. 2 and displayed such as in FIG. 4, the coach identifies this and teaches the bowler grip and approach techniques that compliment this style of play.

Conversely, another bowler is observed naturally exerting more pressure on the inside of his foot during the power step. In a prior example, this was an inconsistency that the coach wanted to cure. However, if this is the bowler's natural tendency, he might be naturally suited for a style of play that utilizes more spin. Based upon the data, the coach teaches the bowler grip and approach techniques that compliment this style of play. These techniques may be very different from the techniques taught to the high-speed player in the previous example.

Although the above examples primarily focus on the plantar pressure distribution during the bowler's power step, similar analysis may be performed on other steps during the bowler's multiple step approach.

Figure 7:
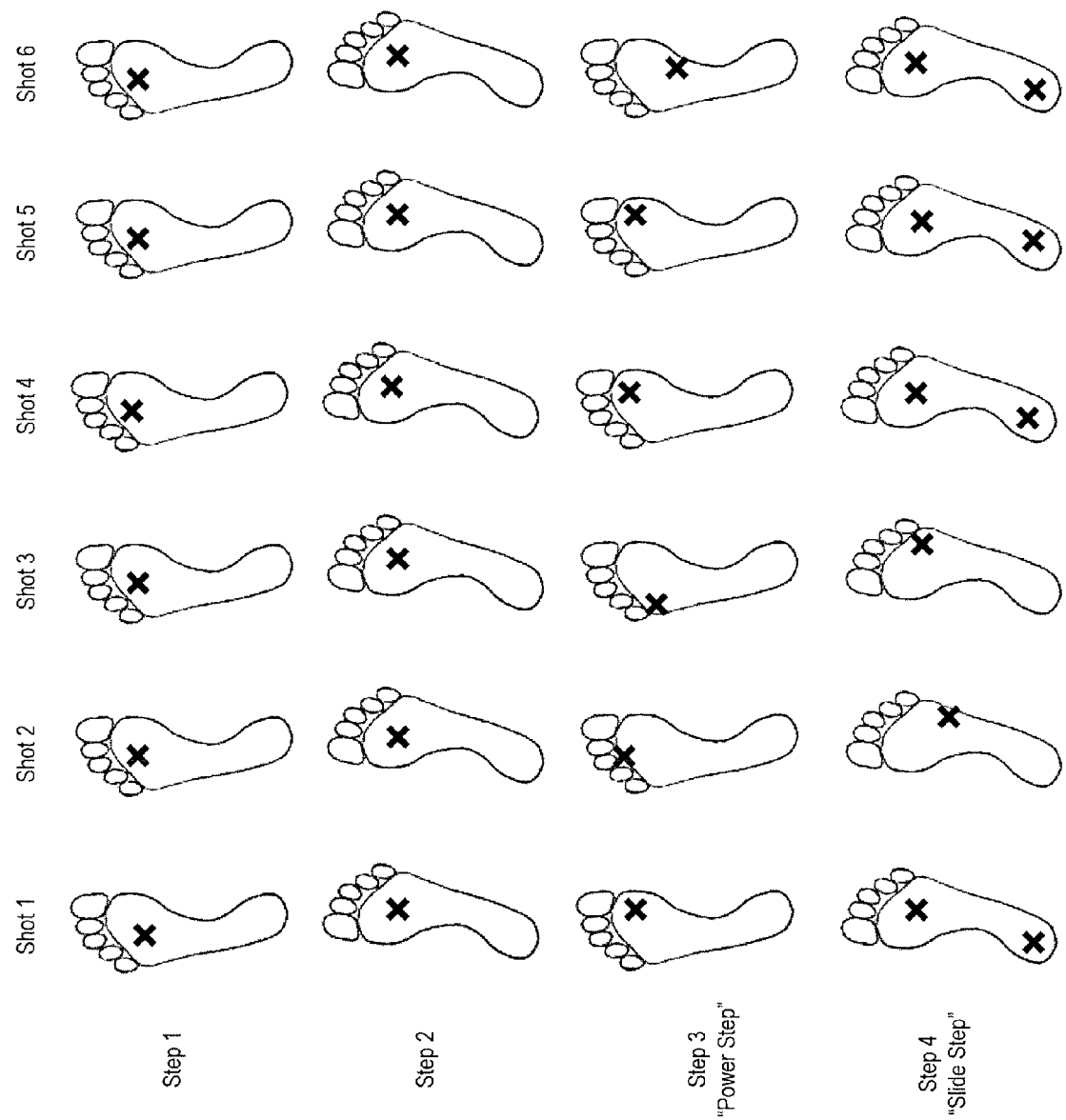
FIG. 7 is an illustration of one example of areas of high pressure detected during each step of a bowler's four step approach. The bowler in this example has repeated the same type of bowling throw six times.

FIG. 7 illustrates another example of using the recorded plantar pressure distribution data such as displayed in FIG. 4 to evaluate a bowler's performance. A coach has instructed the bowler to perform six repetitions of the same type of bowling throw. The left-handed bowler uses a four-step approach beginning with the left foot. FIG. 7 shows a representation of a frame from each subset of frames associated with a step in each of the six repetitions. Areas of high pressure (similar to area 403 in FIG. 4) are marked with an "X."

The bowler is fairly consistent in the first two steps of his approach. In all six repetitions, an area of high pressure is detected near the center of the ball of the foot. In shots 1, 4, and 5, the bowler pushes off of the inside of the ball of the foot during the power step and ends with pressure distributed between the ball of the foot and the heel during the slide step. However, shots 2, 3, and 6 lose consistency at the power step. In shot 2, the bowler pushes off strongly at the front of the ball of the foot. Possibly in an attempt to counteract the excessive force generated during the power step, a large amount of pressure is applied to the outside edge of the foot during the slide step. In shot 3, the bowler's power step focuses pressure on the outside of the ball of the foot and the bowler ends with a similar weight distribution in the slide step. In shot 6, heightened pressure was detected near the arch of the bowler's foot during the power step. The bowler, however, was able to recover and end with his preferred weight distribution in the slide step.

From the data, the coach might conclude that the bowler's natural tendency is to push with the inside of the ball of the foot during the power step and end with an even weight distribution on the ball of the foot and the heel during the slide step (such as in shots 1, 4, and 5). The coach adapts his teaching strategy to focus on inconsistencies in the power step and to train the bowler to replicate the pressure distribution used in shots 1, 4, and 5.

Additional useful quantitative data is also derived from the recorded pressure distributions during the bowler's approach. While a foot is placed on the ground and the bowler applies pressure, the data received by computer 207 (in FIG. 2) reflects the amplitude of the applied pressure. When the foot is lifted and pressure is removed, the data received by computer 207 has significantly lower amplitude. As discussed above in reference to FIG. 3, each step in the bowler's approach is identified by locating the frames where pressure is applied on the foot. Identifying individual steps in the approach allows the data to be used to evaluate both the bowler's approach as a whole and the individual steps of the approach.

TABLE 1 shows the average step timing (in number of frames and in seconds) of an example bowler. Pressure distribution frames were recorded at regular 0.01 second intervals (100 frames per second). The data in TABLE 1 is for a bowler who performed the same type of bowling throw six times. TABLE 1 displays the average number of frames and elapsed time between the beginning of each step for steps 1 through 4. TABLE 1 also shows the average number of frames and elapsed time for which the slide step was held.

TABLE 1

|  | Average Number of Frames | Average Time in Seconds | Standard Deviation (in seconds) |
| --- | --- | --- | --- |
| Step 1 | 67.7 | 0.677 s | 0.0186 s |
| Step 2 | 52.7 | 0.527 s | 0.0103 s |
| Step 3 | 52.2 | 0.522 s | 0.0458 s |
| Step 4 ("Power Step") | 54.3 | 0.543 s | 0.0082 s |
| Length of "Slide Step" | 407.8 | 4.078 s | 2.180 s |

The data in TABLE 1 quantitatively shows a coach that the bowler is very consistent in his step timing. The maximum standard deviation is less than 0.05 seconds (1 frame=0.01 seconds). However, the bowler is somewhat inconsistent in how long the slide step is held (standard deviation of 2.18 seconds—more than half of the average length). With this data, the coach would likely recommend that the bowler work on holding his finishing position until the ball hits the pins.

Repeatability of the approach being the goal, the data displayed in TABLE 1 is used by the bowler and the coach to monitor progress throughout training. Although the bowler in TABLE 1 is already fairly consistent in his approach, the calculated standard deviation would be notably higher for a less skilled bowler. A bowler can quantify his improvement as the standard deviation decreases.

TABLE 2 shows force and pressure measurements for two different bowlers during each bowler's power step and slide step. Each bowler repeated the same type of bowling throw six times. "Force" shows the total amount of force measured in pounds on the foot during the power step or the slide step.

"Max Pressure" shows the highest amount of pressure measured in pounds per square inch at the toe or heel during the power step or the slide step.

TABLE 2

|  | Bowler A | Bowler B |
|---|---|---|
| Power Step - Force (lb-f) | 289.7 lb-f | 278.1 lb-f |
| Power Step - Max. Toe Pressure (psi) | 99.3 psi | 92 psi |
| Slide Step - Force (lb-f) | 287.3 lb-f | 335.3 lb-f |
| Slide Step - Max. Toe Pressure (psi) | 97.7 psi | 72.5 psi |
| Slide Step - Max Heel Pressure (psi) | 81.0 psi | 41.7 psi |

Bowler A weighs approximately 300 pounds. The measured force of 289.7 during the power step tells the coach that the bowler's current shoes do little to absorb the impact of the approach on the bowler's feet. Using plantar pressure distribution data for equipment fitting is discussed in greater detail below. The maximum pressure exerted on the toe during Bowler A's power step is approximately the same as the maximum pressure exerted on the toe during Bowler A's slide. Bowler A's weight is fairly evenly distributed between the heel and the toe during his slide step. From this data, a coach might conclude that this particular bowler tends to plant his foot flat during the slide step and, as a consequence, does not slide far. Conversely, the pressure measured on Bowler B's toe during the slide step is significantly higher than the pressure measured on his heel. From this data, a coach might conclude that Bowler B's slide covers more distance than Bowler A's.

This type of data assists the coach in developing a training program and provides quantitative metrics for monitoring improvement. As discussed above, each bowler has a different style of play. The fact that Bowler A plants his foot at the slide while Bowler B's slide covers more distance does not necessarily mean that one is preferable to the other. However, the quantitative plantar pressure data allows the coach to conclusively observe the balance and pressure exerted on the bowler's foot during the approach. As a bowler's consistency improves, the amplitude and distribution of the measured pressures should become less variant.

In some situations, a coach uses the quantitative data, such as in TABLES 1 and 2, as well as the graphical depiction of plantar pressure distribution as shown in FIG. 4 to evaluate the bowler's performance.

In addition to evaluating the performance of a bowler, in another example, the recorded graphical and quantitative plantar pressure data is used by an equipment fitter to select footwear for a particular bowler. As discussed above in reference to FIG. 3, the equipment fitter equips the bowler's shoes with the plantar pressure distribution sensors as shown in FIG. 1 and instructs the bowler to perform multiple repetitions of the same bowling motion. The equipment fitter then places the plantar pressure distributions sensors in a second pair of shoes and instructs the bowler to repeat the same series of bowling motions with the second pair of shoes. The recorded plantar pressure distribution is analyzed and a pair of shoe is selected based upon the pressure data.

For example, while a bowler is wearing a first pair of shoes, the inconsistent areas of high pressure depicted in FIG. 7 are recorded. While wearing a second pair of shoes, the bowler does not score higher, but the recorded plantar pressure data shows a more consistent weight distribution during the power step and the slide step. As a consequence, the equipment fitter is likely to conclude that the second pair of shoe is better for this bowler even though the bowler's score does not immediately improve.

The equipment fitter also analyzes the step timing, the maximum force and the maximum pressure data. In this example, the bowler performed five repetitions of the same style of bowling throw on the same line while wearing his own bowling shoes. The bowler was instructed to hold the position of the slide step for as long as possible after releasing the ball. The bowler then repeated this series of throws with each of three new bowling shoes. The average time (in seconds) between steps 1 through 4, the duration of the slide step (in seconds), and the maximum force/pressure during the power step and slide step are included in TABLE 3.

TABLE 3

|  | Current Shoe | Shoe #1 | Shoe #2 | Shoe #3 |
|---|---|---|---|---|
| Step 1 Length | 1.100 s | 1.084 s | 1.074 s | 1.140 s |
| Step 2 Length | 0.770 s | 0.728 s | 0.726 s | 0.760 s |
| Step 3 Length | 0.517 s | 0.522 s | 0.492 s | 0.530 s |
| Step 4 Length | 0.493 s | 0.490 s | 0.562 s | 0.510 s |
| Slide Step Length | 2.420 s | 4.230 s | 2.962 s | 4.132 s |
| Power Step - Max. Foot Force (lb-f) | 289.7 lb-f | 235.1 lb-f | 253.9 lb-f | 260.5 lb-f |
| Power Step - Max. Foot Pressure (psi) | 99.3 psi | 112.2 psi | 144.2 psi | 104.6 psi |
| Slide Step - Max. Foot Force (lb-f) | 287.3 lb-f | 241.0 lb-f | 324.4 lb-f | 271.5 lb-f |
| Slide Step - Max. Toe Pressure (psi) | 97.7 psi | 70.8 psi | 100.0 psi | 80.4 psi |
| Slide Step - Max. Heel Pressure (psi) | 81.0 psi | 61.4 psi | 77.4 psi | 69.4 psi |

According to the data in TABLE 3, shoe #1 and shoe #3 absorbed the force exerted by the foot during the slide step better than the bowler's current shoe. The maximum recorded toe and heel pressures during the slide step are also reduced. This improved cushioning appears to benefit the bowler's balance as he is able to hold the position of the slide step significantly longer with shoe #1 and shoe #3—4.23 seconds and 4.13 seconds respectively as compared to 2.42 seconds with the bowler's current shoes. Conversely, although each of the three new shoes is better at absorbing the total force exerted in the power step, the maximum recorded pressure during the power step is higher in each of the new shoes than in the bowler's current shoes.

In addition to identifying which shoe best absorbs total force and maximum pressures, recorded plantar pressure distribution data is analyzed to determine which shoe the particular bowler performs most consistently with. As discussed above, standard deviation in maximum pressures, forces, and step timing indicates the repeatability and consistency of the bowler's approach. If the bowler is looking for a shoe that will immediately improve his consistency, a shoe with the lowest standard deviation of measured data is selected.

For some bowlers, a shoe with less cushioning and, therefore, higher force and pressure measurements allows for more control during the approach. Consequently, some bowlers select a shoe based upon the lowest amount of cushioning that can be used without causing premature soreness in the foot. However, it can take several frames before the bowler detects such soreness. Recorded plantar pressure distribution data reduces the amount of time and discomfort required for such shoe selection.

An equipment fitter determines the level of pressure that causes premature soreness for the particular bowler. This level of pressure can be based, for example, upon averages observed in other bowlers of similar size. The equipment fitter instructs the bowler to perform a bowling motion wearing a new pair of shoes. If the maximum recorded pressure exceeds the threshold, the equipment fitter concludes that the shoes would cause premature soreness in the bowler and tries another pair of shoes.

It should be understood that the constructions and methods described above are exemplary and other configurations and designs are possible. For example, additional components, sensor arrangements, or automated operations may be added to the described constructions and methods without departing from the intended scope. Furthermore, although certain examples are discussed in reference to a specific step during the approach (the power step, for example), the same methods may be applied to other steps unless explicitly stated otherwise. Similarly, the methods and systems described above can be applied to a variety of bowling approaches and are not limited to the four-step or five-step approach style. In some methods described above, increased accuracy can be achieved with a greater number of data sets. Therefore, for example, methods that are described with five or six repetitions of a bowling motion may benefit from even more repetitions. Acts may also be added, removed, or reordered from the examples described above.

Also, it is to be understood that certain terminology used herein is intended to be interpreted broadly. For example, unless explicitly stated otherwise, the terms "first step" and "second step" are used to refer to any two steps in the bowler's approach and are not necessarily limited to a particular sequence. Various features and advantages of the invention are set forth in the following claims.

What is claimed is:

1. A method of analyzing a bowler's performance, the method comprising:
    measuring a first distribution of pressure exerted on a sole of a foot during a first bowling motion;
    recording the first distribution of pressure at regular time intervals during the first bowling motion as a first set of pressure distribution frames;
    measuring a second distribution of pressure exerted on the sole of the foot during a second bowling motion;
    recording the second distribution of pressure at regular time intervals during the second bowling motion as a second set of pressure distribution frames; and
    evaluating the bowler's performance based upon the first and second sets of pressure distribution frames, wherein evaluating the bowler's performance includes:
        detecting a first location of an area of high pressure in a pressure distribution frame from the first set of pressure distribution frames,
        detecting a second location of the area of high pressure in a pressure distribution frame from the second set of pressure distribution frames,
        determining a first direction of ball movement in the first bowling motion;
        determining a second direction of ball movement in the second bowling motion; and
        correlating a difference between the first direction of ball movement and the second direction of ball movement to a difference between the first location of the area of high pressure and the second location of the area of high pressure.

2. The method of claim 1, further comprising:
    identifying a first pressure distribution frame associated with a first step in the first bowling motion; and
    identifying a second pressure distribution frame associated with the first step in the second bowling motion.

3. The method of claim 2, further comprising:
    identifying a first subset of pressure distribution frames associated with the first step in the first bowling motion, the first subset including the first pressure distribution frame; and
    identifying a second subset of pressure distribution frames associated with the first step in the second bowling motion, the second subset including the second pressure distribution frame.

4. The method of claim 2,
    wherein identifying a first pressure distribution frame associated with a first step in the first bowling motion includes identifying the first pressure distribution frame associated with a power step in the first bowling motion; and
    wherein identifying a second pressure distribution frame associated with the first step in the second bowling motion includes identifying the second pressure distribution frame associated with the power step in the second bowling motion.

5. The method of claim 2,
    wherein identifying a first pressure distribution frame associated with a first step in the first bowling motion includes identifying the first pressure distribution frame associated with a slide step in the first bowling motion; and
    wherein identifying a second pressure distribution frame associated with the first step in the second bowling motion includes identifying the second pressure distribution frame associated with the slide step in the second bowling motion.

6. The method of claim 1, further comprising determining a bowler training program based upon the difference between the first and second locations of the area of high pressure.

7. The method of claim 1, further comprising determining a bowler training program based upon the difference between the first and second locations of the area of high pressure and the difference between the first and second directions of ball movement.

8. The method of claim 1, further comprising:
    determining a first elapsed time between a first step and a second step in the first bowling motion based upon the first set of pressure distribution frames; and
    determining a second elapsed time between the first step and the second step in the second bowling motion based upon the second set of pressure distribution frames.

9. The method of claim 8, wherein evaluating the bowler's performance includes identifying a preferred coaching technique based upon differences between the first elapsed time and the second elapsed time.

10. The method of claim 8, wherein evaluating the bowler's performance includes:
    calculating an average elapsed time for a plurality of elapsed times between the first step and the second step, the plurality of elapsed times including the first elapsed time and the second elapsed time; and
    calculating a standard deviation of elapsed times for a plurality of elapsed times between the first step and the second step.

11. The method of claim 10, wherein evaluating the bowler's performance further includes quantifying consistency of the bowler's performance based upon the standard deviation.

12. The method of claim 1, further comprising:
identifying a value of a first maximum pressure exerted during a single step in the first bowling motion; and
identifying a value of a second maximum pressure exerted during the single step in the second bowling motion;
wherein evaluating the bowler's performance includes evaluating a difference between the value of the first maximum pressure and the value of the second maximum pressure.

13. The method of claim 12,
wherein identifying a value of a first maximum pressure exerted during a single step in the first bowling motion includes identifying the value of the first maximum pressure exerted during a power step of the first bowling motion; and
wherein identifying a value of a second maximum pressure exerted during the single step in the second bowling motion including identifying the value of the second maximum pressure exerted during the power step of the second bowling motion.

14. The method of claim 12,
wherein identifying a value of a first maximum pressure exerted during a single step in the first bowling motion includes identifying the value of the first maximum pressure exerted during a slide step of the first bowling motion; and
wherein identifying a value of a second maximum pressure exerted during the single step in the second bowling motion includes identifying the value of the second maximum pressure exerted during the slide step of the second bowling motion.

15. A method of analyzing a bowler's performance, the method comprising:
measuring a first distribution of pressure exerted on a sole of a foot during a first bowling motion;
recording the first distribution of pressure at regular time intervals during the first bowling motion as a first set of pressure distribution frames;
measuring a second distribution of pressure exerted on the sole of the foot during a second bowling motion;
recording the second distribution of pressure at regular time intervals during the second bowling motion as a second set of pressure distribution frames; and
evaluating the bowler's performance based upon the first and second sets of pressure distribution frames, wherein evaluating the bowler's performance includes
detecting a first location of an area of high pressure in a pressure distribution frame corresponding to a power step of the first bowling motion from the first set of pressure distribution frames,
detecting a second location of the area of high pressure in a pressure distribution frame corresponding to a power step of the second bowling motion from the second set of pressure distribution frames,
detecting a third location of the area of high pressure in a pressure distribution frame corresponding to a slide step of the first bowling motion from the first set of pressure distribution frames;
detecting a fourth location of the area of high pressure in a pressure distribution frame corresponding to a slide step of the second bowling motion from the second set of pressure distribution frames;
evaluating a difference between the first location and the second location;
evaluating a difference between the third location and the fourth location;
determining a bowler training program directed towards improving the power step when the difference between the first location and the second location is greater than the difference between the third location and the fourth location; and
determining a bowler training program directed toward improving the slide step when the difference between the third location and the fourth location is greater than the difference between the first location and the second location.

* * * * *